United States Patent [19]
Powles et al.

[11] Patent Number: 5,701,910
[45] Date of Patent: Dec. 30, 1997

[54] ASPIRATION NEEDLE APPARATUS INCORPORATING ITS OWN VACUUM AND METHOD AND ADAPTER FOR USE THEREWITH

[75] Inventors: Trevor J. Powles, Chipstead Surrey, United Kingdom; Mir A. Imran, Palo Alto, Calif.

[73] Assignee: Advanced Cytometric Inc., Sunnyvale, Calif.

[21] Appl. No.: 699,209

[22] Filed: Aug. 19, 1996

Related U.S. Application Data

[63] Continuation of Ser. No. 421,064, Apr. 13, 1995, abandoned.
[51] Int. Cl.$^6$ .................................................. A61B 5/103
[52] U.S. Cl. ........................... 128/764; 128/765; 604/412; 604/415; 604/217; 604/200
[58] Field of Search .................................. 604/240, 411, 604/412, 413, 414, 415, 200, 217, 272, 35, 36, 136, 191; 128/752, 764, 765, 762, 770

[56] References Cited

U.S. PATENT DOCUMENTS

| | | | |
|---|---|---|---|
| 3,484,849 | 12/1969 | Huebner et al. | 604/413 X |
| 3,724,460 | 4/1973 | Gomez et al. | 604/88 |
| 3,797,488 | 3/1974 | Hurschman et al. | 604/136 |
| 4,935,020 | 6/1990 | Broden | 604/411 |
| 5,358,501 | 10/1994 | Meyer | 604/414 |
| 5,496,301 | 3/1996 | Hlavinka et al. | 604/409 |
| 5,518,004 | 5/1996 | Schraga | 182/763 |

Primary Examiner—Michael Powell Buiz
Assistant Examiner—A. T. Nguyen
Attorney, Agent, or Firm—Flehr Hohbach Test Albritton & Herbert LLP

[57] ABSTRACT

An aspiration needle apparatus for collecting cell samples by withdrawing aspirate from tissue in a living body. An aspiration needle is provided which has a flow passage extending from its proximal extremity to its distal extremity. The proximal extremity has a hub end a cell collection chamber therein in communication with the flow passage. A vacuum container is provided which has an enclosed evacuated space evacuated to a subambient pressure to provide a predetermined volume of evacuated space devoid of a solid or a liquid and devoted solely to providing the desired vacuum. The vacuum container is sealed by a penetrable diaphragm providing access to the evacuated space. An adapter mounted on the hub and making a fluid-tight connection therewith is formed to receive the vacuum container. The adapter includes a needle having a flow passage in communication with the flow passage in the aspiration needle. A spring is carried by the adapter. The adapter and the vacuum container are formed so as to permit relative movement between the adapter and the vacuum container against the force of the spring to cause the needle to puncture the diaphragm and thus connect the evacuated space to the aspiration needle to supply subambient pressure to the aspiration needle thereby causing aspirate from the tissue to be drawn into the cell collection chamber.

1 Claim, 3 Drawing Sheets

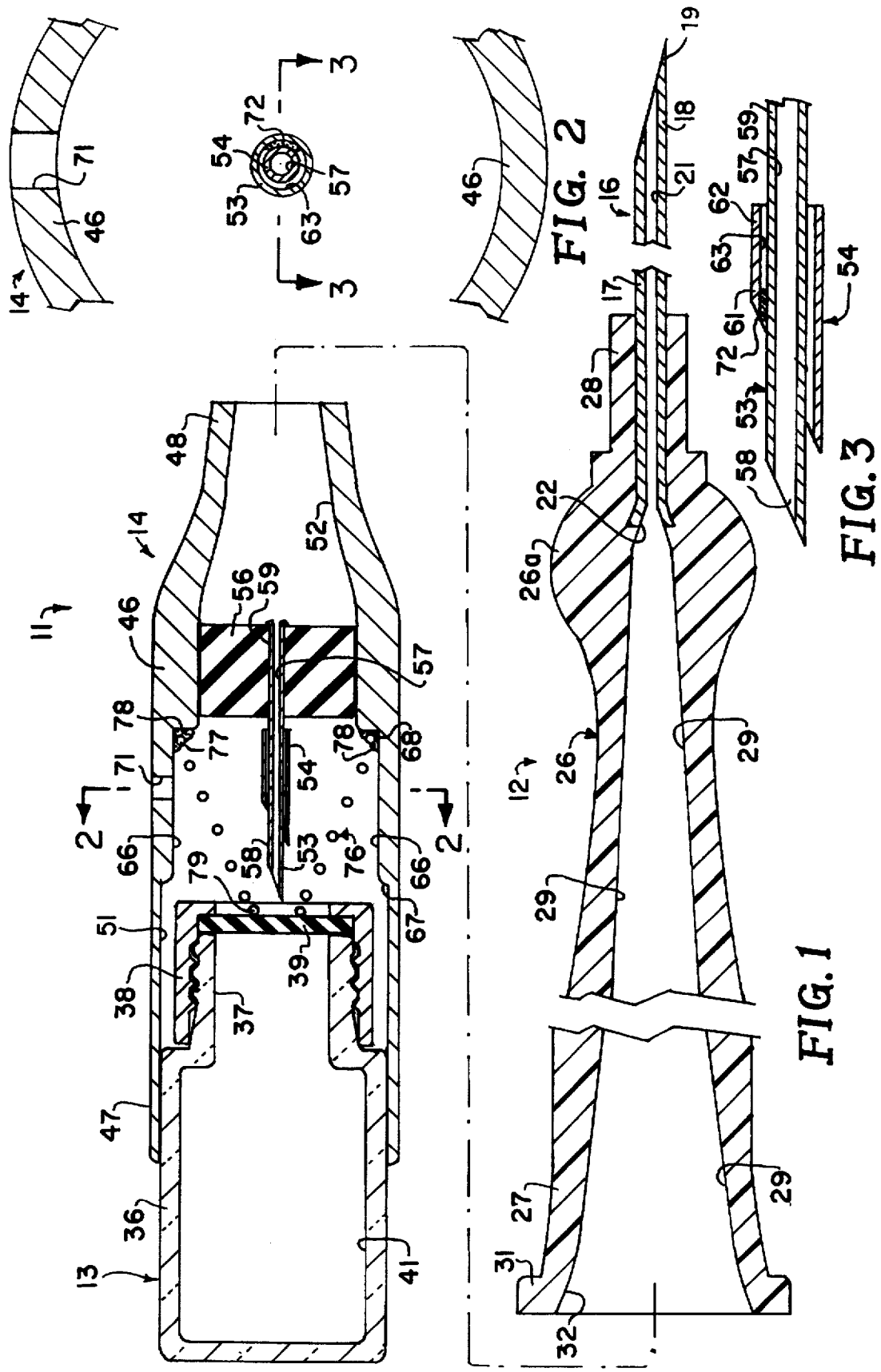

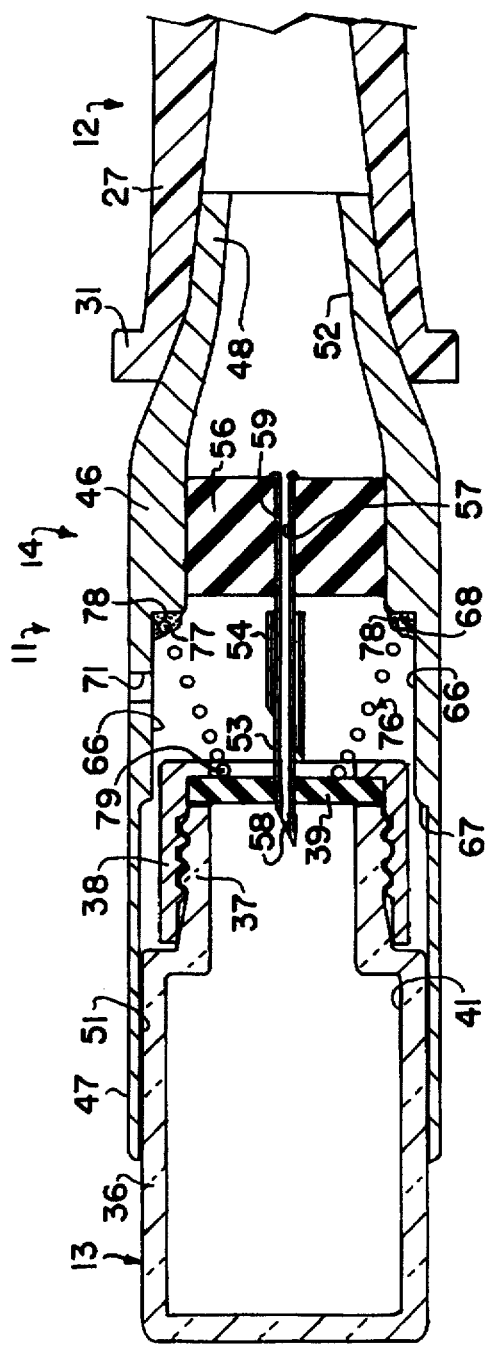
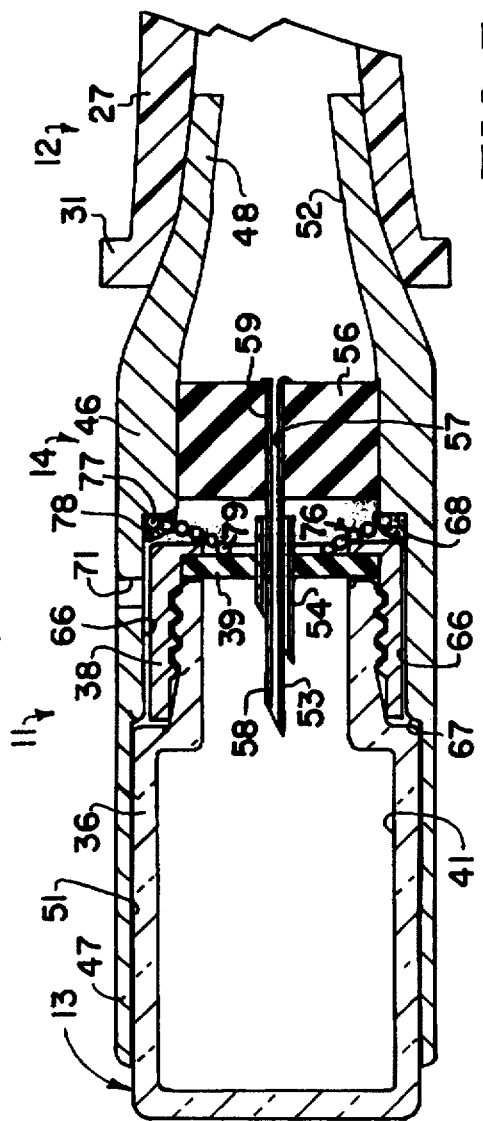
FIG. 4
FIG. 5

ASPIRATION NEEDLE APPARATUS INCORPORATING ITS OWN VACUUM AND METHOD AND ADAPTER FOR USE THEREWITH

This is a continuation of application Ser. No. 08/421,064 filed Apr. 13, 1995 now abandoned.

This invention relates to an aspiration needle apparatus incorporating its own vacuum and a method and adapter for use therewith.

In fine needle aspiration technology, there has been a need for applying a vacuum to the needle to accomplish the aspiration. Typically this has been accomplished by use of a syringe and in certain occasions by the application of a vacuum to the needle by a vacuum pump under the control of the physician performing the aspiration procedure. There is a need for a simplified apparatus for accomplishing fine needle aspiration.

In general, it is an object of the present invention to provide an aspiration needle apparatus incorporating its own vacuum and a method and adapter for use therewith.

Another object of the invention is to provide a removable adapter which can be utilized for mating an aspiration needle to a vacuum container.

Another object of the invention is to provide an apparatus and method and adapter for use therewith which makes it possible to readily establish a vacuum condition in the needle apparatus and to thereafter break the vacuum.

Another object of the invention is to provide an adapter of the above character which can be repeatedly used.

Another object of the invention is to provide an aspiration needle apparatus of the above character in which first and second needles are provided for first communicating with the vacuum and thereafter for breaking the vacuum.

Additional objects and features of the invention will appear from the following description in which the preferred embodiments are set forth in detail in conjunction with the company drawings.

FIG. 1 is a side elevational view in section of an aspiration needle apparatus incorporating its own vacuum which includes the aspiration needle, an adapter and a vacuum container.

FIG. 2 is an enlarged cross-sectional view taken along the line 2—2 of FIG. 1.

FIG. 3, is a cross-sectional view taken along the line 3—3 of FIG. 2.

FIG. 4 is a view similar to that shown in FIG. 1 but showing the vacuum in the vacuum container being applied to the needle.

FIG. 5 is a view similar to FIG. 4 but showing the vacuum to the needle being broken.

Figure 6:
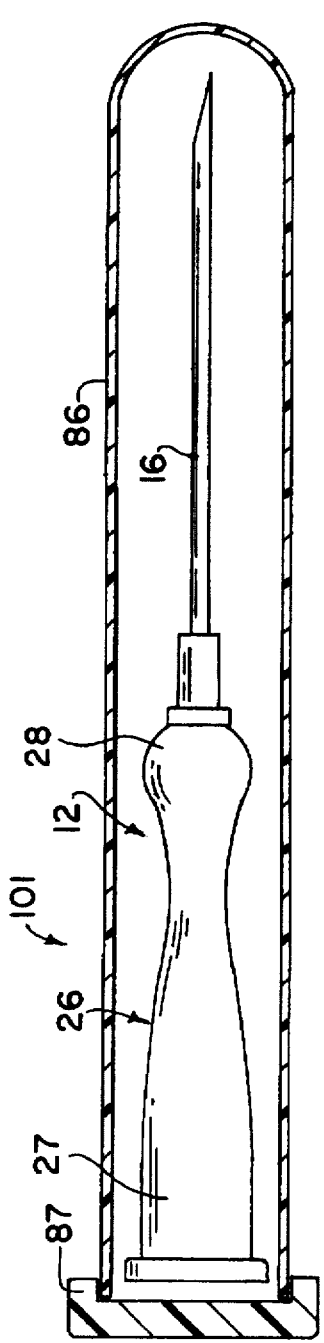
FIG. 6 is a side-elevational view in section showing an aspiration needle with a collected cell sample in a sealed container for transportation to a laboratory.

In general the aspiration needle apparatus of the present invention is comprised of an aspiration needle having proximal and distal extremities with a flow passage extending from the proximal extremity to the distal extremity. A hub is mounted on the proximal extremity of the aspiration needle and has a recess therein in communication with the flow passage in the needle. A vacuum container is provided which encloses an evacuated space and has a penetrable diaphragm carried thereby providing access to the evacuated space. The apparatus also includes an adapter having proximal and distal extremities with the distal extremity being removably mounted on the hub and making a fluid-tight connection with the recess in the hub. The adapter is provided with a body having a flow passage extending from the proximal extremity to the distal extremity of the adapter. The proximal extremity is formed so that it is capable of mating with the vacuum container. The adapter includes first and second needles which are adapted upon relative movement between the adapter and the vacuum container between first and second positions to selectively permit the first needle in the first position to cause a vacuum to be applied from the vacuum container to the recess in the hub and the flow passage in the hub to cause an aspirate to be drawn into the needle and in the second position to permit the second needle to break the vacuum.

More in particular as shown in FIGS. 1–3 of the drawings, the aspiration needle apparatus 11 incorporating its own vacuum consists of an aspiration needle 12, a vacuum container 13 and an adapter 14 for mating the vacuum container 13 to the aspiration needle 12.

The aspiration needle 12 is of the type described in copending application Ser. NO. 08/228,551 filed Apr. 15, 1994 consisting of a rigid elongate tubular member 16 formed of a suitable material such as stainless steel having a length of 2 to 8 centimeters and of a suitable diameter as for example 23 gauge. The rigid elongate tubular member 16 is provided with proximal and distal extremities 17 and 18 in which the distal extremity is sharpened to form a needle point. The rigid elongate tubular member 16 is provided with a flow passage 21 extending from the distal extremity 18 to the proximal extremity 17. The proximal extremity 17 is flared outwardly to provide a funnel-shaped recess 22 leading into the flow passage 21.

A body 26 is mounted on the proximal extremity 17 of the rigid tubular member 16 and is formed of a suitable plastic as for example ULTEM. The body 26 is provided with proximal and distal extremities 27 and 28. The body 26 is provided with a conical chamber 29 extending from the proximal extremity 27 to the distal extremity 28. The body 26 is provided with a spherical enlarged portion 26a which circumscribes the conical chamber 29 in the region immediately adjacent the funnel shaped recess 22 which serves as a convex lens to magnify that portion of the container for viewing aspirate as hereinafter described. The body 26 is provided with a hub 31 on the proximal extremity 27 that has a tapered conical recess 32 which adjoins the conical chamber 29. The body 26 is provided with an annular recess 33 proximal of the enlarged portion 26a which is adapted to be engaged by fingers of the hand for controlling and movement of the needle for a purpose hereinafter described.

The vacuum container 13 is in the form of a vacuum bottle 36 formed of a suitable material such as glass. The glass bottle is of a conventional construction and is generally cylindrical in shape and is provided with a neck 37 of reduced diameter that has been threaded to receive a threaded cap 38. The cap 38 is provided with a self-sealing diaphragm or membrane 39 formed of a suitable self sealing elastomeric material which can be readily penetrated by a conventional surgical needle. The vacuum container 13 encloses an evacuated space 41 of a suitable size as for example 15 to 30 milliliters and preferably approximately 20 milliliters. This space 41 as shown in FIG. 1 is devoid of a solid or liquid and is devoted solely to providing the desired vacuum. The space 41 can be evacuated to a vacuum below ambient or atmospheric or a sub-ambient pressure ranging from 15 to 20" of mercury.

The adapter 14 consists of generally of a cylindrical body 46 which can be formed of a suitable material such as a transparent plastic, i.e., a polycarbonate or an acrylic. The body 46 is provided with proximal and distal extremities 47 and 48. The distal extremity 48 is necked down as shown in FIG. 1 and is adapted to be removably mounted on the hub 31 of the body 26 to form a fluid-tight seal therewith. Cooperative mating means is provided on the proximal extremity 48 of the body 46 and on the vacuum container 13. Thus as shown in FIG. 1 the proximal extremity 47 is provided with a cylindrical recess 51 which is adapted to receive the vacuum container 13. A flow passage 52 is provided extending from the cylindrical recess 51 through the distal extremity 48 so that it is in communication with the conical recess 29 of the aspiration needle 12.

Needle means is carried by the adapter body 46 for establishing a connection between the flow passage 52, the interior of the vacuum container 13 first for supplying a vacuum to the flow passage 52 and thereafter to break the vacuum being supplied to the flow passage 52. Such needle means is shown in FIG. 1 and consists of first and second needles 53 and 54 formed of a suitable material such as stainless steel. As shown, the first and second needles 53 and 54 are carried by the body 46 and are disposed within the passage 52. The first needle 53 is mounted in a resilient plug or block 56 frictionally retained in the flow passage 52 of the body 46 and formed of a suitable material such as rubber through which the first needle 53 extends. The first needle is provided with a flow passage 57 which extends from a proximal sharpened tip 58 to a distal extremity 59 extending through the plug 56 and opening into the flow passage 52 in the body 46.

The second needle 54 is provided with a proximal extremity 61 and a distal extremity 62. As shown particularly in FIGS. 1 and 2, the second needle 54 is sized so that it can be coaxially mounted on the exterior of the first needle 53 and form an annular flow passage 63 extending from the proximal extremity 61 to the distal extremity 62 and opening into a chamber 66 that is defined by annular shoulders 67 and 68 and which is open to the atmosphere through a hole 71. As can be seen, the proximal extremity 61 of the second needle 54 is sharpened as shown and is distal of the proximal extremity 58 of the first needle 53 by a suitable distance as for example ½" for a purpose hereinafter described. The second needle 54 is supported on the first needle 53 in a suitable manner such as by use of an adhesive or solder 72 within the annular passage 63 as shown particularly in FIG. 2.

Yieldable means in the form of a spring 76 is provided within the chamber 66 and has a larger distal or base end 77 engaging the shoulder 68 and retained in engagement therein by suitable means such as an adhesive 78. The smaller or proximal end 79 of the spring 76 yieldably engages the diaphragm or membrane 39 so as to retain the membrane or diaphragm 39 out of engagement with the sharp end of the first needle 53.

Operation and use of the aspiration needle apparatus 11 may now be briefly described. Let it be assumed that it is desired to perform an aspiration procedure after a physician or surgeon has found a palpable breast tumor by utilizing the apparatus of the present invention for obtaining a cell sample from the breast tumor by withdrawing aspirate from the breast tumor. The apparatus 11 is assembled with the adapter 14 inserted into the conical recess 32 of the needle. The vacuum container 13 is disposed in the adapter 14 with the proximal extremity 58 of the needle 53 distal of the membrane 39 as shown in FIG. 1. The surgeon using one hand for locating the palpable breast tumor utilizes the other hand to grasp the aspiration needle apparatus 11 by two fingers as for example the thumb and forefinger to grasp the annular recess 33 of the aspiration needle 12 and pushes the needle to penetrate the skin of the breast and to enter into the breast tissue and to lodge the distal extremity of the aspiration needle 12 within the tumor. As soon as the surgeon is assured that the needle 12 is lodged into the appropriate position within the tumor.

The surgeon or physician using the forefinger of the hand holding the aspiration needle apparatus 11 engages the vacuum container 13 and presses it distally against the force of the spring 76 to cause relative movement between the adapter 14 and the vacuum container 13 to a first position to cause the sharpened proximal extremity 58 of the first needle 53 to puncture the diaphragm or membrane 39 carried by the container 36 to expose the evacuated space 41 to the interior flow passage 57 of the first inner needle 53 (see FIG. 4). This in turn exposes the flow passage in the body 46 and the conical chamber 29 in the aspiration needle 12 and the flow passage 21 in the elongate tubular member 16 to create a sub-ambient condition within the tumor to cause cells of the tumor to be withdrawn from the tumor as an aspirate into the flow passage 21 and to bring the aspirate into the chamber 29 where the entrance of the aspirate into the chamber can be observed visually through the magnifying lens framed by the spherical portion 26a as shown in FIG. 3.

As soon as it has been ascertained that sufficient aspirate has been drawn into the chamber 29, the sub-ambient pressure being applied to the rigid elongate tubular member can be terminated or broken by the physician pushing the vacuum container 13 in the form of a vacuum bottle 36 and additional distance proximally against the force of the yieldable spring 76 to a second position so that the second needle 54 has its proximal extremity 61 penetrating through the diaphragm 39 as shown in FIG. 5. As soon as the proximal extremity 61 penetrates into the space 41, atmospheric air can enter into the space passing through the hole 71 in the body 46 and into the annular flow passage 63 in the second needle 54 and into the space 41. Thus it can be seen as soon as the second needle 54 punctures the diaphragm 39 the sub-ambient pressure applied to the aspiration needle 12 will be abruptly terminated so that no further aspirate is withdrawn from the tumor.

When the cell sample has been collected in the aspirate within the chamber 29, the aspirate remains within the chamber 29. As soon as the desired cell sample has been collected, the aspiration needle 12 can be withdrawn from the tumor with the adapter 14 and the vacuum container in place. Alternatively if desired, the adapter 14 containing the vacuum container 13 can be removed before withdrawing the aspiration needle 12.

Thereafter, the aspiration needle 12 can be handled in the manner hereinbefore described in connection With the copending application Ser. No. 08/228,551 filed Apr. 15, 1994. As described therein, the aspirate can be discharged onto slides which are shipped to laboratory for analysis or alternatively, the entire needle with the cell sample with the aspirate therein can be supplied to the laboratory for analysis. Thus, as shown in FIG. 6, the aspiration needle 12 with the collected cell sample therein can be placed in a test tube-like container 86 formed of a suitable material such as plastic and sealed with a removable cap 87 for transportation to a laboratory for analysis.

Figure 8:
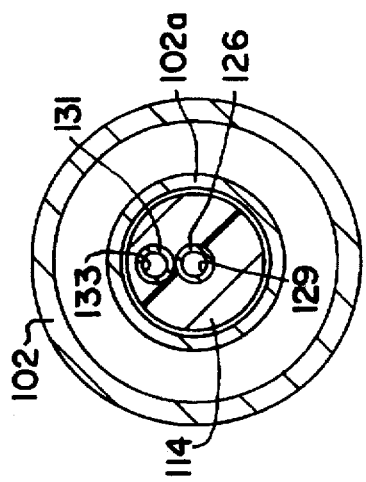
FIG. 8 is a cross sectional view taken along the lines 8—8 of FIG. 5.

Another embodiment of an aspiration needle apparatus incorporating the present invention is shown in FIGS. 5 and 8. As shown therein, the needle aspiration apparatus 101 consists of aspiration needle 12 identical to that hereinbefore described and a vacuum container 102 and an adapter 103. As shown, the vacuum container 102 can be in the form of a metal canister or container that is in the form of an elongate cylinder and having an internal cylindrical portion 102a disposed coaxially therein. The cylindrical portion 102a defines a cylindrical chamber or recess 107 extending axially of the cylindrical portion 102a which opens through an opening 108 open to the atmosphere provided in one end of the metal container 102. The other end of the cylindrical recess 107 is open through an opening 109 into an interior evacuated annular space 111 in the vacuum container 102 through a self-sealing diaphragm or membrane 112 mounted therein by suitable means such as an adhesive (not shown) to close off that end of the cylindrical recess 107. The cylindrical recess 107 is sized so it can serve as a female adapter for receiving the cylindrical male adapter 103 in the form of a cylindrical body 114 formed of a suitable material such as a transparent plastic of the type hereinbefore described and is provided with the proximal and distal extremities 116 and 117. It is provided with a flow passage 118 extending from the proximal extremity 116 to the distal extremity 117. It is also provided with an additional flow passage 119 that is generally parallel to the passage 118 and extends from the proximal extremity to a point intermediate the proximal and distal extremities 116 and 117 and is in communication with a sidewise extending port 121 that is positioned so it is always open to the atmosphere for a purpose hereinafter described.

Figure 7:
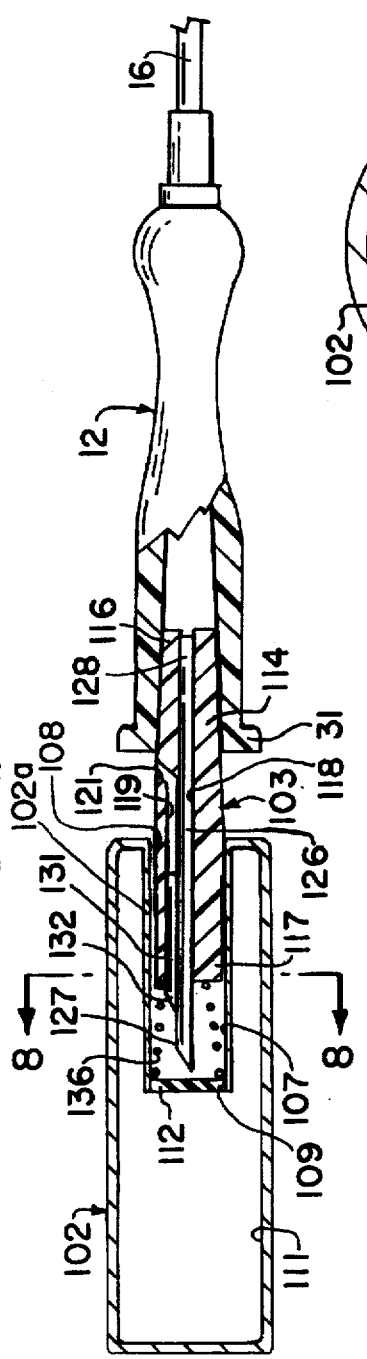
FIG. 7 is a side elevational view of another embodiment of the present invention.

A first needle 126 formed of a suitable material such as stainless steel which has a sharpened tapered proximal extremity 127 and a distal extremity 128 is disposed within the flow passage 118 and is retained therein in a suitable manner such as by an adhesive (not shown). The first needle 126 is provided with a flow passage 129 that extends from the proximal extremity 127 to the distal extremity 128 of the needle and opens into the flow passage 118. Similarly, a second needle 131 having a sharpened proximal extremity 132 and a distal extremity 134 is mounted within the body 114 by suitable means such as an adhesive (not shown). It has a flow passage 133 extending from the sharpened proximal extremity 132 to the distal extremity 134 which is in communication with the flow passage 119 that opens to the atmosphere through the port 121 as hereinbefore described. As shown in FIG. 7, the proximal extremities 116 and 127 of the first and second needles 126 and 131 are staggered so that the first needle 126 extends proximally for a suitable distance as for example approximately ¼ to ½" beyond the proximal extremity 127 so that the first and second needles 126 and 131 can sequentially penetrate the diaphragm 112 as hereinafter described. The proximal extremity of the body 116 is tapered as shown so that it can make a tight friction fit with the hub 31 of the aspiration needle 12 to provide a fluid-tight seal therebetween.

A conical coil spring 136 is disposed within the cylindrical recess 107 and is secured therein by suitable means such as an adhesive (not shown) and extends distally from the diaphragm 112 and is adapted to be engaged by the adapter 103 when it is inserted into the cylindrical recess 107. The coil spring 136 serves to prevent inadvertent puncturing of the diaphragm 112 by the first and second needles 126 and 131.

Operation and use of the aspiration needle apparatus 101 as shown in FIGS. 7 and 8 is very similar to that shown in FIG. 1 with the exception that the vacuum container 13 shown in FIG 1 is in the form of a male member adapted to mate with an adapter 14 which is constructed as a female member providing a chamber 66 for receiving the vacuum container 13. Conversely, with the embodiment shown in FIGS. 7 and S, the vacuum container 102 is constructed as a female member having a cylindrical recess 107 therein adapted to receive an adapter 103 which is constructed in the form of a male member adapted to mate with the cylindrical recess 107. Thus, as can be seen in the arrangement shown in FIG. 1, the first and second needles 53 and 54 are coaxially disposed with respect to each other whereas in the embodiment shown in FIG. 7, the first and second needles 126 and 131 are disposed side by side.

In operation of the apparatus shown in FIGS. 7 and 8, when the aspiration needle has been positioned so that the distal extremity 18 of the aspiration needle 12 is disposed within the tumor, the vacuum container 102 can be pressed forwardly or proximally against the force of the conical coil spring 136 to a first position to cause the proximal extremity 127 of the first needle to penetrate the diaphragm 112 and to expose the aspiration needle 12 to the sub-ambient pressure provided in the vacuum container 102 to cause aspirate to be drawn into the chamber of the aspiration needle 12 in the manner hereinbefore described. When a sufficient sample has been collected, the vacuum container 102 can be further depressed to cause the proximal extremity 132 of the second needle 132 to puncture the diaphragm to expose the evacuated space 111 in the vacuum container 12 to ambient through the port 121 to break the sub-ambient condition being applied to the aspiration needle 12 to thereby terminate collection of aspirate. Thereafter, the needle aspiration apparatus 101 can be removed and the sample collected in the aspiration needle treated in the manner hereinbefore described.

It is apparent from the foregoing that there has been provided an aspiration needle apparatus 11 which facilitates collection of aspirate and cell samples as for example in tumors and the like. This collection is enhanced because it eliminates the necessity for the physician or surgeon doing the procedure to utilize a syringe or other vacuum source to create the necessary sub-ambient condition in the aspiration needle. By utilizing a pre-packaged vacuum container to supply the desired sub-ambient condition to the needle for an appropriate period of time, the collection of the appropriate cell sample is greatly enhanced. Thus it is possible to readily collect cell samples without the necessity of having a syringe or other accessory devices as for example a vacuum pump to supply the sub-ambient condition. Also by providing a vacuum container having a predetermined volume of evacuated space, it is possible to program the sub-ambient pressure applied to the aspiration needle 12 to also predetermine the maximum amount of time that a sub-ambient pressure will be applied to the aspiration needle. In addition, the aspiration needle apparatus of the present invention is relatively simple. It can be readily manufactured. If desired, it can be supplied in kit form.

What is claimed is:

1. An aspiration needle apparatus for collecting cell samples by withdrawing aspirate from tissue in a living body comprising an aspiration needle having proximal and distal extremities and having a flow passage extending from the proximal extremity to the distal extremity, the proximal extremity having a hub formed thereon, said hub having a cell collection chamber therein in communication with the flow passage in the aspiration needle, a vacuum container having an enclosed evacuated space evacuated to a subambient pressure which provides a predetermined volume of evacuated space devoid of a solid or a liquid and devoted solely to providing the desired vacuum and sealed by a penetrable diaphragm providing access to the evacuated space, an adapter mounted on the hub and making a fluid-tight connection therewith, said adapter being formed to receive said vacuum container and receiving said vacuum container, said adapter including needle means carried thereby having a flow passage therein in communication with the flow passage in the aspiration needle, yieldable means carried by the adapter, said adapter and said vacuum container being formed so as to permit relative movement between the adapter and the vacuum container against the force of the yieldable means to cause the needle means to puncture the diaphragm of the vacuum container to connect the evacuated space having a subambient pressure in the vacuum container to the aspiration needle to supply the subambient pressure to the aspiration needle to cause aspirate from the tissue to be drawn into the cell collection chamber.

* * * * *

UNITED STATES PATENT AND TRADEMARK OFFICE
CERTIFICATE OF CORRECTION

PATENT NO. : 5,701,910

DATED : December 30, 1997

INVENTOR(S) : Powles et al.

It is certified that error appears in the above-indentified patent and that said Letters Patent is hereby corrected as shown below:

On the title page, item [73], after "Advanced", replace "Cytometric" with -- Cytometrix --

Signed and Sealed this

Third Day of March, 1998

Attest:

BRUCE LEHMAN

*Attesting Officer*  *Commissioner of Patents and Trademarks*